(12) United States Patent
Ooya et al.

(10) Patent No.: US 9,585,985 B2
(45) Date of Patent: Mar. 7, 2017

(54) METHOD FOR COATING SYNTHETIC POLYMER SURFACE WITH BIOPOLYMER

(75) Inventors: Shouji Ooya, Kanagawa (JP); Tetsuo Hiratou, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1211 days.

(21) Appl. No.: 12/519,119

(22) PCT Filed: Dec. 13, 2007

(86) PCT No.: PCT/JP2007/001391
§ 371 (c)(1),
(2), (4) Date: Jun. 12, 2009

(87) PCT Pub. No.: WO2008/072378
PCT Pub. Date: Jun. 19, 2008

(65) Prior Publication Data
US 2010/0028691 A1 Feb. 4, 2010

(30) Foreign Application Priority Data
Dec. 13, 2006 (JP) .................. 2006-335275

(51) Int. Cl.
| | | |
|---|---|---|
| *A61L 27/34* | (2006.01) | |
| *A61F 2/06* | (2013.01) | |
| *D01D 5/08* | (2006.01) | |
| *B41J 3/407* | (2006.01) | |
| *A61K 49/00* | (2006.01) | |
| *A61K 39/395* | (2006.01) | |

(52) U.S. Cl.
CPC ............. *A61L 27/34* (2013.01); *A61F 2/06* (2013.01); *A61K 39/395* (2013.01); *A61K 49/00* (2013.01); *B41J 3/407* (2013.01); *D01D 5/08* (2013.01); *Y10T 428/31551* (2015.04); *Y10T 428/31768* (2015.04); *Y10T 428/31786* (2015.04); *Y10T 428/31971* (2015.04)

(58) Field of Classification Search
CPC ............ A61F 2/06; D01D 5/08; A61K 39/395
USPC .... 424/9.6, 145.1, 85.1; 347/106; 623/1, 12; 606/192; 264/465; 514/2
See application file for complete search history.

(56) References Cited

U.S. PATENT DOCUMENTS

| | | | | |
|---|---|---|---|---|
| 5,591,225 A | * | 1/1997 | Okuda | .............. 623/1.49 |
| 5,693,085 A | * | 12/1997 | Buirge | .......... A61F 2/0022 |
| | | | | 606/192 |
| 7,662,332 B2 | * | 2/2010 | Chu | .............. D01D 5/0069 |
| | | | | 264/465 |
| 2006/0181592 A1 | * | 8/2006 | Gandasasmita et al. | ..... 347/106 |
| 2006/0204441 A1 | * | 9/2006 | Atala et al. | ............. 424/9.6 |
| 2007/0160606 A1 | * | 7/2007 | Heavner | ........... C07K 16/241 |
| | | | | 424/145.1 |

FOREIGN PATENT DOCUMENTS

| | | |
|---|---|---|
| JP | 60-080461 A | 5/1985 |
| JP | 62-207466 A | 9/1987 |
| JP | 05-269198 A | 10/1993 |
| JP | 10-507470 A | 7/1998 |
| JP | 11-004883 A | 1/1999 |
| JP | 11-510399 A | 9/1999 |
| JP | 2004-523484 A | 8/2004 |
| JP | 2006-263144 A | 10/2006 |
| JP | 2007-301213 A | 11/2007 |
| JP | 2007-301214 A | 11/2007 |
| WO | 96/08149 A1 | 3/1996 |
| WO | 96/12058 A1 | 4/1996 |
| WO | 02/40242 A1 | 5/2002 |

OTHER PUBLICATIONS

Grafe et al., Polymeric Nanofibers and Nanofiber Webs: A New Class of Nonwovens, Sep. 2002, INTC 2002: International Nonwovens Technical Conference.*
PST, Synthesis and Characterization of Macromolecules, Chapter 10, Gel Permeation Chromatography, 2013, pp. 61-77.*
Lundgren et al., Fluid Shear Disruption of Cultred Endothelium: The Effect of Cell Species Fibronectin Cross-linking and Supporting Polymer, 1986, Transactions of the American Society of Artificial Internal Organs, vol. XXXII, pp. 334-338.*
An English-language International Preliminary Report on Patentability dated Jun. 25, 2009.
Office Action dated Nov. 6, 2012 on Japanese Application No. JP 2008-549204.

* cited by examiner

*Primary Examiner* — Dah-Wei D Yuan
*Assistant Examiner* — Andrew Bowman
(74) *Attorney, Agent, or Firm* — Sughrue Mion, PLLC

(57) ABSTRACT

An object to be solved by the present invention is to provide a method for preparing a composition prepared by firmly coating the surface of a material with a biopolymer, and a composition prepared by this method wherein the surface of a material is firmly coated with a biopolymer. The present invention provides a method for coating with a biopolymer, which comprises coating the surface of a synthetic polymer with a biopolymer dissolved in a solvent comprising an organic fluorine compound.

2 Claims, No Drawings

METHOD FOR COATING SYNTHETIC POLYMER SURFACE WITH BIOPOLYMER

TECHNICAL FIELD

The present invention relates to a method for coating a structure prepared using a synthetic polymer with a biopolymer, and a composition prepared by coating the surface of a synthetic polymer with a biopolymer, which is obtained by the above method.

BACKGROUND ART

Synthetic polymers are broadly used as medical materials. Synthetic polymers are used because they offer easy control of the strengths and structures of materials and easy control of any molding and processing. However, these synthetic polymers have drawbacks in that they often lack affinity for living organisms and lack the inherent bioactivity of biopolymers, for example. To enhance the affinity of the synthetic polymers for living organisms, cells have been caused to adhere to the surfaces of such synthetic polymers, surface treatment has been performed for such synthetic polymers, or such synthetic polymers have been coated or bound with biopolymers (Journal of Biomaterial Science, Polymer Edition. 1993; 4 (3): 217-34, JP Patent Publication (Kokai) No. 61-82760 A (1986); JP Patent Publication (Kokai) No. 4-15063 A (1992); JP Patent Publication (Kohyo) No. 4-503311 A (1992)).

Moreover, JP Patent Publication (Kohyo) No. 11-510399 A (1999) discloses a biomaterial having a thrombus-resistant surface and a method for producing the same. The thrombus-resistant surface is composed of a coating layer of chitosan and 1 or more types of bioactive substance (e. g., polyvinyl alcohol capable of forming a polymer blend with chitosan).

Biopolymers that are polymers existing in living organisms are generally soluble in water. Accordingly, when the surfaces of synthetic polymers are coated with biopolymers, the surface of the synthetic polymer is generally coated with an aqueous solution containing biopolymers by various coating methods such as dip coating or spin coating (Brash, Trans. Am. Soc. Artif. Int. Organs, p. 69, 1974).

When a surface coated with biopolymers with the use of water is embedded within a living organism, biopolymer-derived characteristics are imparted to the surface-coated product at the early implantation stage (e.g., approximately several hours). However, as the time for implantation passes, the problem of the peeling off of biopolymers emerges.

Meanwhile, a technique for binding the functional groups on the surfaces of synthetic polymers to the functional groups of biopolymers using a condensing agent or the like has been studied. According to this technique, the chemical structure is partially altered via application of chemical bonds to biopolymers. Hence, the functions of the biopolymers may be decreased, or any side effect may occur.

Organic fluorine compounds represented by 1,1,1,3,3,3-hexafluoro-2-propanol (HFIP) or trifluoroethanol (TFE) dissolve proteins such as collagen and gelatin. JP Patent Publication (Kohyo) No. 2002-531182 A discloses that a protein matrix for tissue construction is prepared by dissolving the protein and alkyl ester of hyaluronic acid in HFIP and molding the resultant. Also, JP Patent Publication (Kohyo) No. 2004-532802 A and JP Patent Publication (Kokai) No. 2004-321484 A disclose that a structure of protein is prepared by electrospinning. However, only a structure of collagen or gelatin is prepared with the use of this technique, and it is not used for coating of material surface with biopolymers.

Non-patent document 1: Journal of Biomaterial Science, Polymer Edition. 1993; 4 (3): 217-34
Non-patent document 2: Brash, Trans. Am. Soc. Artif. Int. Organs, p. 69, 1974)
Patent document 1: JP Patent Publication (Kokai) No. 61-82760 A (1986)
Patent document 2: JP Patent Publication (Kokai) No. 4-15063 A (1992)
Patent document 3: JP Patent Publication (Kohyo) No. 4-503311 A (1992)
Patent document 4: JP Patent Publication (Kohyo) No. 11-510399 A (1999)
Patent document 5: JP Patent Publication (Kohyo) No. 2004-532802 A
Patent document 6: JP Patent Publication (Kokai) No. 2004-321484 A

DISCLOSURE OF THE INVENTION

Object to be Solved by the Invention

An object of the present invention is to address the above problems of the conventional technology. Specifically, an object to be solved by the present invention is to provide a method for preparing a composition prepared by firmly coating the surface of a material with a biopolymer, and a composition prepared by this method wherein the surface of a material is firmly coated with a biopolymer.

Means for Solving the Object

As a result of intensive studies in order to achieve the above object, the present inventors have discovered that a biopolymer can be firmly coated by coating the surface of a synthetic polymer with an organic fluorine compound solution containing a biopolymer so as to partially immerse the biopolymer into the surface of a synthetic polymer. Thus, the present inventors have completed the present invention.

The present invention provides a method for coating with a biopolymer, which comprises coating the surface of a synthetic polymer with a biopolymer dissolved in a solvent comprising an organic fluorine compound.

Preferably, the biopolymer is a protein, a polysaccharide (for example, glycosaminoglycan or proteoglycan), or a derivative thereof.

Preferably, the biopolymer contains at least one selected from the group consisting of collagen, gelatin, albumin, laminin, casein, fibroin, fibrin, chitin, chitosan, fibronectin, vitronectin, urokinase, thrombomodulin, antithrombin III, hyaluronic acid, hyaluronic acid ester (hyaluronate), heparin, and chondroitin sulfate.

Preferably, the protein is a human-, bovine-, pig-, or fish-derived protein, or a gene recombinant protein.

The biopolymer may be chemically modified.

Preferably, the chemical modification involves modifying a biopolymer with another compound via an ester bond, an amide bond or an ether bond.

Preferably, the synthetic polymer contains at least one selected from the group consisting of polyorthoester, polylactic acid, polyglycolic acid, and a copolymer thereof, polyethylene terephthalate (PET), and polyurethane (PU).

Preferably, the organic fluorine compound is alcohol, ketone, or carboxylic acid.

Preferably, the organic fluorine compound is 1,1,1-hexafluoro-2-propanol, trifluoroethanol, hexafluoroacetone, trifluoroacetic acid, or pentafluoropropionic acid.

Another aspect of the present invention provides a composition prepared by coating the surface of a synthetic polymer with a biopolymer, wherein the ratio of the biopolymer to the synthetic polymer continuously decreases, depending on the depth from the composition surface.

Preferably, the composition of the present invention is produced by the method for coating with a biopolymer according to the present invention as mentioned above.

EFFECT OF THE INVENTION

According to the present invention, the surface of a synthetic polymer can be firmly coated with a biopolymer without causing chemical changes due to introduction of chemical bonds. Thus, the present invention makes it possible to achieve long-standing biocompatibility of a synthetic polymer, which is difficult to achieve by coating according to the conventional technology. For example, it can be expected that cell adhesiveness can be significantly improved by coating the non-cell-adhesive surface of polylactic acid with cell-adhesive gelatin or collagen. It can also be expected that blood compatibility can be significantly improved by coating with blood-compatible albumin. Also, since the surface of a substrate can be firmly coated with a biopolymer, long-standing stability of performance can be expected without causing any peeling off of the coating.

Furthermore, when a surface that is in contact with water is coated with a general biopolymer, crosslinking is carried out using a crosslinking agent or the like. With the use of the present invention, a biopolymer can be kneaded into the surface of a synthetic polymer without crosslinking. Therefore, a firm biopolymer surface can be prepared on the surface of a synthetic polymer, so that the resultant contains no crosslinking agent that may cause inflammation.

PREFERRED EMBODIMENTS OF THE INVENTION

The present invention will be described in more detail below.

The method for coating with a biopolymer according to the present invention is characterized by coating the surface of a synthetic polymer with a biopolymer dissolved in a solvent comprising an organic fluorine compound.

A biopolymer to be used in the present invention is not particularly limited, as long as it is a biologically derived polymer, and it is preferably a protein, a polysaccharide (e.g., glycosaminoglycan or proteoglycan), or a derivative thereof. More preferably, the biopolymer is collagen, gelatin, albumin, laminin, casein, fibroin, fibrin, chitin, chitosan, fibronectin, vitronectin, urokinase, thrombomodulin, antithrombin III, hyaluronic acid, hyaluronic acid ester (hyaluronate), heparin, or chondroitin sulfate. Further preferably, the biopolymer is collagen, gelatin, albumin, laminin, casein, fibroin, fibrin, fibronectin, or vitronectin. Particularly preferably, the biopolymer is collagen, gelatin, albumin, casein, fibroin, or chitosan. Most preferably, the biopolymer is collagen or gelatin. The protein origin is not particularly limited. Any human-, bovine-, pig-, or fish-derived proteins or gene recombinant proteins can be used. As a gene recombinant gelatin, those described in EU 1014176A2 or U.S. Pat. No. 6,992,172 can be used, but the examples are not limited thereto. Also, the biopolymer may be partially hydrolyzed.

The form of the biopolymer is not particularly limited. However, the biopolymer may be in the form of a non-crosslinked product, a physically or chemically crosslinked product, a chemically modified product, or a mixture thereof. Preferably, the biopolymer is in the form of a non-crosslinked product or a chemically modified product. Most preferably, the biopolymer is in the form of a non-crosslinked product. When the biopolymer is chemically modified, specific examples of such biopolymer include a biopolymer containing an ester bond, an amide bond or an ether bond between the biopolymer and another compound.

In addition, it is not required that the biopolymer be present alone within a structure prepared with the use of the biopolymer, and the biopolymer may be contained as a partial component in the structure.

The biopolymer dissolved in a solvent comprising an organic fluorine compound is used. Types of organic fluorine compound to be used in the present invention are not particularly limited, as long as both the above biopolymer and a synthetic polymer explained as follows are dissolved. The organic fluorine compound is preferably a C1-8 organic fluorine compound, more preferably a C1-6 organic fluorine compound, and further more preferably a C1-3 organic fluorine compound. Preferably, the organic fluorine compound is alcohol, ketone, or carboxylic acid. Specific examples of the organic fluorine compound include 1,1,1-hexafluoro-2-propanol (hereinafter, also referred to as HFIP), trifluoroethanol, hexafluoroacetone, trifluoroacetic acid, and pentafluoropropionic acid. Most preferably, the organic fluorine compound is hexafluoro-2-propanol or trifluoroethanol. The organic fluorine compound may be used alone or may be used in combination with a solvent compatible therewith. The compatible solvent is preferably water. The composition of the organic fluorine compound in a solvent, which is used for coating, is not particularly limited, as long as the present invention can be performed. Preferably, the composition of the organic fluorine compound in a solvent is 0.0001% or more, more preferably 0.1% or more, and further preferably 10% or more.

Furthermore, the concentration of the biopolymer upon coating with the biopolymer is not particularly limited, as long as the present invention can be performed, and the concentration is substantially 0.0001% or more and 20% or less, and more preferably 0.01% or more and 2% or less. The amount of the biopolymer contained in a synthetic polymer can be controlled by varying the concentration of the biopolymer upon coating.

When a biopolymer dissolved in a solvent comprising an organic fluorine compound is coated and the solvent remains on the surface of the biopolymer for long time, the solvent penetrates the inside of the synthetic polymer. This may cause alteration in the characteristics of the bulk of the synthetic polymer. Therefore, the organic fluorine compound is desirably removed after coating. The organic fluorine compound preferably has a boiling point of 0° C. or more and 150° C. or less, more preferably a boiling point of 10° C. or more and 100° C. or less, and most preferably a boiling point of 15° C. or more and 80° C. or less.

The process for removing a solvent after coating of a biopolymer dissolved in the solvent comprising the organic fluorine compound is generally natural drying. However, if necessary, washing with water, heating, and vacuum operation may be applied. The process for removing a solvent is not particularly specified, but is realistically carried out at a temperature which is equal to or is lower than a temperature at which a synthetic polymer is thermally modified. Preferably, the temperature is 0° C. or more and 150° C. or less, more preferably, 0° C. or more and 100° C. or less, further more preferably 0° C. or more and 80° C. or less, and most preferably 0° C. or more and 70° C. or less. Humidity may contribute to shape-keeping properties or the like and should be varied depending on the solvent, the biopolymer and the application employed herein. The content of the organic fluorine compound in a structure after the process for removing the solvent is not particularly specified, but is desirably low in consideration of medical applications. The content is preferably 1% or less and more preferably 0.1% or less in the total composition.

A synthetic polymer to be used in the present invention is not particularly limited, as long as the present invention can be performed, and it is preferably a polymer soluble in an organic fluorine compound. The synthetic polymer is more preferably a polymer having a urethane bond, an ester bond, an ether bond or a carbonate bond, or a vinyl polymer, or a copolymer thereof. More preferably, the synthetic polymer is polyorthoester, polylactic acid, polyglycolic acid, or a copolymer thereof, poly($\epsilon$-caprolactone), polyhydroxyalkanoate (PHA), polyvinyl pyrrolidone (PVP), polymethylene carbonate (TMC), polyurethane, segmented polyurethane, polyether polyurethane, or polyethylene terephthalate (PET). Further preferably, the synthetic polymer is poly($\epsilon$-caprolactone), polyurethane, segmented polyurethane, polyether polyurethane, or PET. The synthetic polymer may be contained as a component of a structure, and may be contained in a mixture with other materials. The percentage by weight of the synthetic polymer in the structure is not particularly limited, as long as the present invention can be performed, and is substantially 10% or more, preferably 300% or more, more preferably 50% or more, and most preferably 80% or more.

The molecular weight of the synthetic polymer is not particularly limited and is generally 1 KDa or more and 10 MDa or less, preferably 5 KDa or more and 500 KDa or less, and most preferably 10 KDa or more and 100 KDa or less. Moreover, the synthetic polymer may be subjected to crosslinking and/or chemical modification.

The form of the synthetic polymer is not particularly limited, as long as the present invention can be performed. Examples of the form include gel, sponge, film, non-woven fabric, fibers (tubes), and particles. The synthetic polymer can be used in any form. Examples of such form include pyramidal, conical, rectangular cylindrical, circular cylindrical, spherical, and spindle-shaped structure, and structure produced by using molds with any desired shapes. Preferably, the form is a rectangular cylindrical, circular cylindrical, or spindle-shaped structure, or a structure produced using a mold with any desired shape. More preferably, the form is a pyramidal, conical, rectangular cylindrical, or circular cylindrical structure. Most preferably, the form is a rectangular cylindrical or circular cylindrical structure. For example, when an artificial vascular lumen surface is coated with albumin, an HFIP solution containing albumin is added to an internal surface of PET tube, and coating and drying can be carried out while the tube is rotated.

The size of the structure comprising the synthetic polymer is not particularly limited. When the structure is in the form of gel, sponge or non-woven fabric, the size is preferably 500 centimeters square or less, preferably 100 centimeters square or less, particularly preferably 50 centimeters square or less, and most preferably 10 centimeters square or less. When it is formed into a fiber (tube), the diameter of the fiber or tube (or one side of the cross section thereof) is 1 nm or more and 10 cm or less, preferably 1 nm or more and 1 cm or less, more preferably 1 nm or more and 100 µm or less, particularly preferably 1 nm or more and 1 µm or less, and most preferably 1 nm or more and 10 nm or less. In addition, the length thereof is not particularly limited. The length thereof is preferably 10 µm or more and 100 m or less, more preferably 100 µm or more and 10 m or less, further preferably 1 mm or more and 1 m or less, and most preferably 1 cm or more and 30 cm or less. When the structure is in the form of particles, the particle size (diameter) preferably ranges from 1 nm to 1 mm, more preferably ranges from 10 nm to 200 µm, further preferably ranges from 50 nm to 100 µm, and particularly preferably ranges from 100 nm to 10 µm.

The thickness of the structure comprising the synthetic polymer is not particularly limited. The thickness is preferably 1 nm or more, more preferably 10 nm or more, further preferably 100 nm or more, even more preferably 1 µm or more, yet more preferably 10 µm or more, and most preferably 100 µm or more.

In the present invention, the surface of the synthetic polymer is coated with a biopolymer dissolved in a solvent comprising an organic fluorine compound, so that the synthetic polymer is partially dissolved in the organic fluorine compound. Accordingly, in the composition prepared by coating the surface of a synthetic polymer with a biopolymer, the ratio of the biopolymer to the synthetic polymer continuously decreases, depending on the depth from the composition surface. Specifically, according to the method of the present invention, a composition prepared by coating the surface of a synthetic polymer with a biopolymer can be produced, wherein the ratio of the biopolymer to the synthetic polymer continuously decreases depending on the depth from the composition surface. The composition having such structure is also within the scope of the present invention.

The present invention is hereafter described in greater detail with reference to the following examples, although the present invention is not limited thereto.

EXAMPLES

Example 1

Albumin Coating of PET Film

PET film (2 cm×2 cm) was coated with an aqueous solution (400 µL) containing 0.1% albumin or a solution (400 µL) of 1,1,1-hexafluoro-2-propanol (HFIP), followed by 1 day of natural drying. The film was immersed in water at 37° C. and then shaken for 1 hour. The sweepback contact angle of water of the film was measured. The sweepback contact angle in the case of the film prepared by coating with the aqueous solution was 65±5 degrees which is similar to that in the case of untreated PET film (untreated PET film: 68±4 degrees). On the other hand, the sweepback contact angle of water of the film prepared by coating with the HFIP solution was significantly decreased to be 11±6 degrees. It can be said that albumin coating was effectively achieved on the PET film with the use of HFIP as a solvent for coating. Furthermore, HFIP partially dissolved the PET surface, so that the concentration of albumin to PET was continuously decreased.

Example 2

Gelatin Coating of PET Film

Gelatin coating of PET film was carried out by using the process used in Example 1. Similar to Example 1, when water was used as a solvent for coating, the sweepback contact angle of water after washing with water was found to be similar to that of an untreated case. On the other hand, when trifluoroethanol was used as a solvent, the sweepback contact angle of water was significantly decreased to be 13±6 degrees. It can be said that PET could be effectively coated with gelatin with the use of TFE as a solvent for coating.

INDUSTRIAL APPLICABILITY

According to the present invention, the surface of a synthetic polymer can be firmly coated with a biopolymer without causing chemical changes due to introduction of chemical bonds.

The invention claimed is:

1. A method for coating with a biopolymer, which comprises coating the surface of a synthetic polymer with a solution of a biopolymer dissolved in a solvent comprising an organic fluorine compound to prepare a composition, whereby the surface of the synthetic polymer is partially dissolved by the organic fluorine compound, wherein:

the synthetic polymer is a polymer which is used as medical material and is embedded within a living organism;

in the composition, the ratio of the biopolymer to the synthetic polymer continuously decreases depending on the depth from a surface of the composition;

the surface of the synthetic polymer is coated with the biopolymer without causing chemical changes due to introduction of chemical bonds;

the biopolymer is gelatin or albumin;

the organic fluorine compound is 1,1,1-hexafluoro-2-propanol, trifluoroethanol, hexafluoroacetone, trifluoroacetic acid, or pentafluoropropionic acid; and the synthetic polymer contains at least one selected from the group consisting of polylactic acid, polyglycolic acid, polyethylene terephthalate, and polyurethane.

2. The method according to claim 1, wherein the protein is a human-, bovine-, pig-, or fish-derived protein, or a gene recombinant protein.

* * * * *